(12) United States Patent
Chow et al.

(10) Patent No.: US 10,545,214 B2
(45) Date of Patent: Jan. 28, 2020

(54) ELECTRON PARAMAGNETIC RESONANCE DOSIMETER, METHODS OF MANUFACTURE, AND METHODS OF USE

(71) Applicant: ADA Foundation, Chicago, IL (US)

(72) Inventors: Laurence C. Chow, Potomac, MD (US); Shozo Takagi, Gaithersburg, MD (US); Marc Frederic Desrosiers, Waynesboro, PA (US)

(73) Assignee: ADA FOUNDATION, Chicago, IL (US)

( * ) Notice: Subject to any disclaimer, the term of this patent is extended or adjusted under 35 U.S.C. 154(b) by 0 days.

(21) Appl. No.: 16/431,872

(22) Filed: Jun. 5, 2019

(65) Prior Publication Data

US 2019/0285714 A1      Sep. 19, 2019

Related U.S. Application Data

(62) Division of application No. 15/068,943, filed on Mar. 14, 2016, now abandoned.

(60) Provisional application No. 62/133,018, filed on Mar. 13, 2015.

(51) Int. Cl.
*G01R 33/60* (2006.01)
*G01T 1/04* (2006.01)
*A61B 6/10* (2006.01)
*G01N 24/10* (2006.01)

(52) U.S. Cl.
CPC ............... *G01R 33/60* (2013.01); *A61B 6/10* (2013.01); *A61B 6/107* (2013.01); *G01N 24/10* (2013.01); *G01T 1/04* (2013.01)

(58) Field of Classification Search
CPC ........... G01R 33/60; G01T 1/04; A61B 6/107; A61B 6/10; G01N 24/10
See application file for complete search history.

(56) References Cited

U.S. PATENT DOCUMENTS 5,149,368 A * 9/1992 Liu ..................... A61K 6/033
106/35

OTHER PUBLICATIONS

Oliveira et al. (2004). "Development of an EPR dosimetry system based on hydroxyapatite in the therapy dose level". Proceedings of the 9 Brazilian congress on medical physics; 3 Iberian Latin American and Caribbean congress on medical physics, (p. v). Brazil pp. 1-5) (Year: 2004).*

* cited by examiner

*Primary Examiner* — Dennis White

(57) ABSTRACT

An electron paramagnetic resonance device includes a crystalline, emission-sensitive mass and a housing containing the device. The mass includes structurally incorporated carbonate content in a range of about 3% by weight to about 10% by weight of the mass, one or more structurally incorporated non-calcium metallic cations, and one or more structurally incorporated phosphate anions. When irradiated with a known source, the EPR device may function as a reference. When unirradiated, the EPR may function as a dosimeter. As a dosimeter, the EPR device may be used as a personal dosimeter or as a monitor for inanimate objects being subjected to radiation sources. The EPR dosimeter may be used for both gamma radiation and neutron radiation measurements.

20 Claims, 5 Drawing Sheets

ELECTRON PARAMAGNETIC RESONANCE DOSIMETER, METHODS OF MANUFACTURE, AND METHODS OF USE

RELATED APPLICATIONS

This patent application is a division of U.S. patent application Ser. No. 15/068,943 filed Mar. 14, 2016, entitled "Electron Paramagnetic Resonance Dosimeter, Methods of Manufacture, and Methods of Use," which claims priority to provisional patent application 62/133,018 filed Mar. 13, 2015, entitled "Electron Paramagnetic Dosimeter, Dosimetry Reference, Methods of Manufacture, and Methods of Use." The disclosures of these applications are incorporated by reference.

BACKGROUND

Certain materials, when exposed to ionizing radiation, can be stimulated to emit a measurable signal that may be used to estimate the received radiation dose. Certain of these materials may be incorporated into a dosimeter that is worn or carried by an individual to measure the individual's exposure. A thermoluminescent dosimeter (TLD) is an example. To be effective in monitoring radiation exposure, the TLD must be worn or carried by the individual during periods of possible radiation exposure. For medical/industrial applications of ionizing radiation, dosimeters are used to assess the quality of the treatment or process.

Dosimetry systems and techniques exist that exploit radiation-induced signals emanating from biological materials. In some of these techniques, the signals may be measured in vivo. Examples of such techniques include electron paramagnetic resonance (EPR) dosimetry, which may be used to measure signals in teeth, fingernails, toenails, bone and hair. These techniques hold out the promise for screening (i.e., as part of a triage effort), at a point-of-care facility, large populations groups that may have been exposed to ionizing radiation.

EPR dosimetry is based on the following: (1) ionizing radiation generates unpaired electrons (e.g., free radicals) in proportion to the absorbed dose; (2) EPR dosimetry can selectively and sensitively detect and determine the number of unpaired electrons; and (3) the unpaired electrons can persist in some tissues, such as teeth and nails, with enough stability so as to be measured by EPR dosimetry weeks to years after radiation exposure.

SUMMARY

A dosimeter for EPR dosimetry systems includes a carbonated hydroxyapatite cement formed by mixing a cement powder and a cement liquid in a ratio of a range of about 0.5 to 5.0 powder-to-liquid ratio. The cement powder comprises one or more calcium phosphate compounds and one or more carbonate compounds. The cement liquid comprises a phosphate solution. The cement, when irradiated by a radiation source, is capable of producing a measurable signal comprising a spectrally clean EPR spectrum. Furthermore, the measurable signal is proportional to the received radiation dose.

An electron paramagnetic resonance (EPR) device includes a crystalline, emission-sensitive mass and a housing containing the device. The mass includes structurally incorporated carbonate content in a range of about 3% by weight to about 10% by weight of the mass, one or more structurally incorporated non-calcium metallic cations, and one or more structurally incorporated phosphate anions. When irradiated with a known source, the EPR device may function as a reference. When unirradiated, the EPR may function as a dosimeter. As a dosimeter, the EPR device may be used as a personal dosimeter or as a monitor for inanimate objects being subjected to radiation sources. The EPR dosimeter may be used for both gamma radiation and neutron radiation measurements.

DESCRIPTION OF THE DRAWINGS

The Detailed Description refers to the following Figures, in which like numerals refer to like items, and in which.

DETAILED DESCRIPTION

Figure 1:
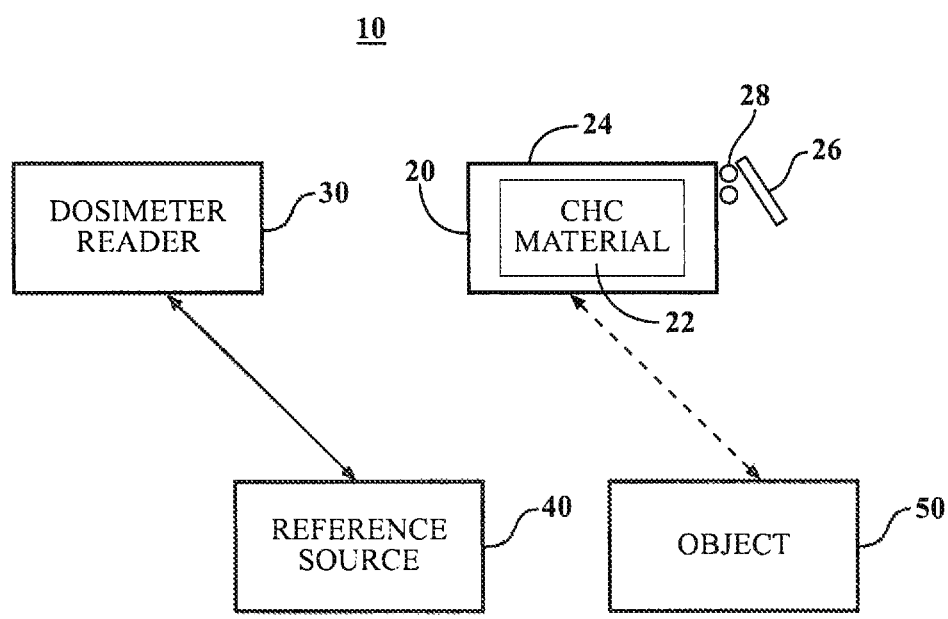
FIG. 1 is a simplified block diagram of an example EPR dosimetry system.

Disclosed herein a dosimeter that uses a novel material to capture ionizing radiation and provide for reliable measurement of received dose. Also disclosed are methods of manufacture and methods of use. The dosimeter is based on the following concepts developed by the inventors to this application:

A carbonated hydroxyapatite cement (CHC) may serve as an inexpensive, easily formed material for the dosimeter.

For a given crystallinity of the CHC material, the EPR signal produced by a given irradiation dose increases with increasing carbonate content in the apatite.

For a given carbonate content, the EPR signal produced by a given irradiation dose decreases with decreasing crystallinity of the CHC material.

For a given crystallinity and carbonate content, the EPR signal increases with the absorbed radiation dose.

The crystallinity of CHC decreases with increasing carbonate content.

For a given carbonate content, the crystallinity increases, within certain limits, with increasing calcium substitution by sodium.

Starting with these hypotheses, the inventors developed several self-hardening cement compositions, and subjected the compositions to various tests, described herein, to prove these hypotheses.

In the course of this analysis and testing, the inventors discovered other surprising and unexpected properties and hence uses for the cement compositions. These other properties and uses are disclosed herein.

In the course of the investigations, the inventors discovered that certain of these cement compositions could function well as an EPR dosimeter. More specifically, and in a herein described embodiment, the EPR dosimeter is based on the surprising discovery that a special synthetic carbonated hydroxyapatite cement (CHC) material in the form of a hardened mass of any desired dimension may, when exposed to certain ionizing radiation, produce an EPR signal. These materials are pure CHC without any binders. The materials may be in the shape of a cylinder, disc, block, plate, or film. Further, the CHC samples are chemically stable and have adequate mechanical strength and surface integrity to be used for any EPR dosimetry system.

In addition, the CHC compositions may have the potential to be used with other than photon irradiation, including irradiation from neutron sources.

The novel CHC precursor compositions include cement powder that consists of one or more calcium phosphate compounds selected from a group that includes monocalcium phosphate anhydrous, monocalcium phosphate monohydrate, dicalcium phosphate anhydrous, dicalcium phosphate dihydrate, amorphous calcium phosphate, α-tricalcium phosphate, β-tricalcium phosphate, and tetracalcium phosphate.

The compositions further include one or more soluble carbonate compounds (such as sodium carbonate, sodium bicarbonate, potassium carbonate, potassium bicarbonate, ammonium carbonate) or sparingly soluble carbonate compounds (such as calcium carbonate, iron carbonate, magnesium carbonate, and zinc carbonate).

Optionally, the cement powder also may include one or more of the following;

Sparingly soluble calcium compounds (such as calcium lactate, calcium sulfate, calcium oxide, and calcium hydroxide).

Sparingly soluble phosphate compounds (such as iron phosphate, magnesium phosphate, zinc phosphate).

Soluble phosphate compounds (such as sodium phosphate and potassium phosphate).

One or more water reducing agents such as sodium citrate and citric acid.

Median particle sizes of each of the cement powder components should be in the range of 0.1 to 150 μm.

Cement liquid in an aqueous phosphate solution with total phosphate concentration in the range of about 0.005 to 2.5 mol/L. The liquid may further contain gelling agents such as cellulose and a water reducing agent such as citrate.

Samples of the cement compositions were prepared according to the following:

The cement powder and liquid were mixed with a powder/liquid ratio in the range of about 0.5 to 5 to produce a uniform paste.

The paste was then placed in a mold of desired shape and dimensions.

After one day, the hardened sample was removed from the mold. The demolded sample was immersed in a physiological-like fluid for 5 days to allow the cement setting reaction to complete. Optionally, the formed sample can be fired to produce a ceramic material with enhanced properties.

A fully set CHC sample is an impure hydroxyapatite with a low to medium crystallinity compared to pure hydroxyapatite (NIST standard reference material). The material contains a structurally incorporated carbonate content in the range of 0.05 to 12 mass %. The material also may contain structurally incorporated non-calcium metallic cations (such as $Na^+$) and acid phosphate anion, $HPO_4^{2-}$.

Example 1

In Example 1, a cement powder consisted of tetracalcium phosphate, dicalcium phosphate, and sodium bicarbonate to allow the CHC product to contain 3% by weight of carbonate. The cement liquid was 0.5 mol/L $Na_2HPO_4$ solution. Cement paste with a powder/liquid ratio of 3 was prepared and placed in a mold to produce discs (6 mm D×3 mm H). The hardened discs were analyzed by XRD and FTIR for phase composition and carbonate contents, respectively. The CHC discs were then gamma-ray irradiated to 10 kGy (10,000 Gy) with a NIST-calibrated Co-60 source and their EPR characteristics were determined.

XRD showed that the only phase present in hardened CHC samples was low crystalline HA. FTIR analysis revealed carbonate bands at 1413 $cm^{-1}$ and 1455 $cm^{-1}$ indicating that the HA contained type-b carbonate similar to the carbonate in apatitic biomaterials. After gamma-ray irradiation, the CHC discs showed reproducible EPR signals. The 3% carbonate samples exhibited a spectrally perfect example of the radical.

Example 2

Figure 5:
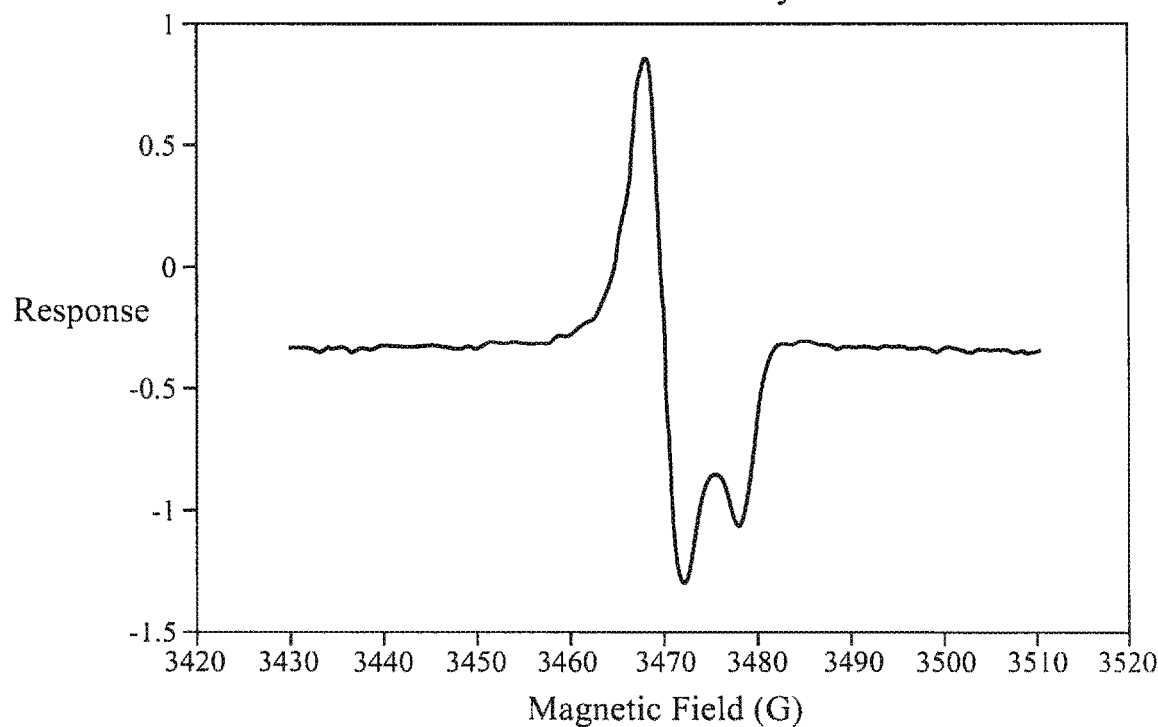
FIG. 5 illustrates an EPR spectrum of carbonated a hydroxyapatite cement sample with 3% carbonate content.

In Example 2, the materials were as described in example 1, except that the carbonate content was increased to 10% by weight. The materials were formed into hardened discs and the discs were subjected to the same testing as described for Example 1. The 10% carbonate sample also produced EPR signals. However, the signals are not spectrally clean (FIG. 5 illustrates a spectrally clean EPR signal), making the material less suitable for use as high accuracy dosimeters or dosimeter reference sources.

The following table illustrates additional potential components of a carbonated hydroxyapatite cement.

TABLE

| Cement Powder | Expected Product | Cement Liquid |
| --- | --- | --- |
| $Ca_4(PO_4)_2O$ + $CaHPO_4$ + $NaHCO_3$ | $Ca_{5-x}Na_x(PO_4)_{3-x}(CO_3)_xOH$ | $Na_2HPO_4$ solution |
| $Ca_4(PO_4)_2O$ + $CaHPO_4$ + $KHCO_3$ | $Ca_{5-x}H_x(PO_4)_{3-x}(CO_3)_xOH$ | $K_2HPO_4$ solution |
| $3CaHPO_4$ + $2CaCO_3$ + NaF | $Ca_{5-x}Na_x(PO_4)_{3-x}(CO_3)_xOH_{1-y}F_y$ | $Na_2HPO_4$ solution |
| $3CaHPO_4$ + $2CaCO_3$ + KF | $Ca_{5-x}H_x(PO_4)_{3-x}(CO_3)_xOH_{1-y}F_y$ | $K_2HPO_4$ solution |

Rather than forming a cement (i.e., CHC), the carbonated hydroxyapatite powder, as noted herein, may be fired or sintered to form a hardened mass, which in turn, may serve as a component of an EPR dosimeter or as an EPR reference source.

Figure 6:
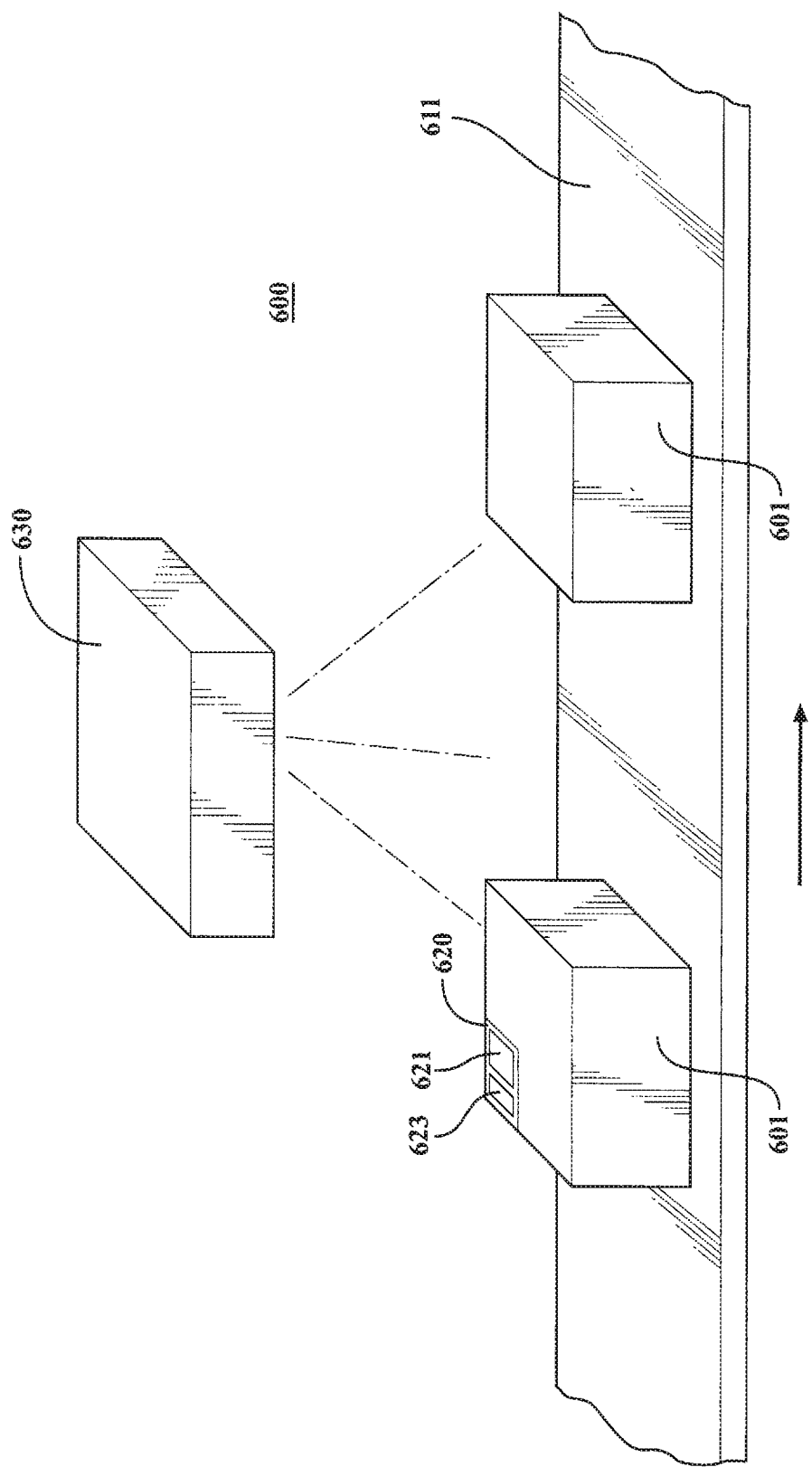
FIG. 6 illustrates an example use of EPR dosimetry using a carbonated hydroxyapatite dosimeter.

FIG. 1 is a simplified diagram of an example CH-based EPR dosimetry system. In FIG. 1, EPR dosimetry system 10 includes EPR dosimeter 20, dosimeter reader 30, and reference source 40. The EPR dosimeter 20 includes carbonated hydroxyapatite cement (CHC) material 22 that receives a radiation dose and, when read in an appropriate dosimeter reader produces a measurable signal such as those shown in FIG. 4. As disclosed herein, the CHC material 22 is a carbonated hydroxyapatite cement formulated as described in Examples 1 and 2. The CHC material 22 may be enclosed in structure or housing 24 that protects the material and that allows the dosimeter 20 to be effectively attached to object 50 whose cumulative radiation dose is to be monitored and measured. For example, the structure 24 may include a clip 26 that enables the dosimeter 20 to be attached to the clothing of a human subject. FIG. 6, described later, illustrates other structures for enclosing, protecting, and attaching an EPR dosimeter to an object whose cumulative radiation dose is to be monitored.

Figure 2:
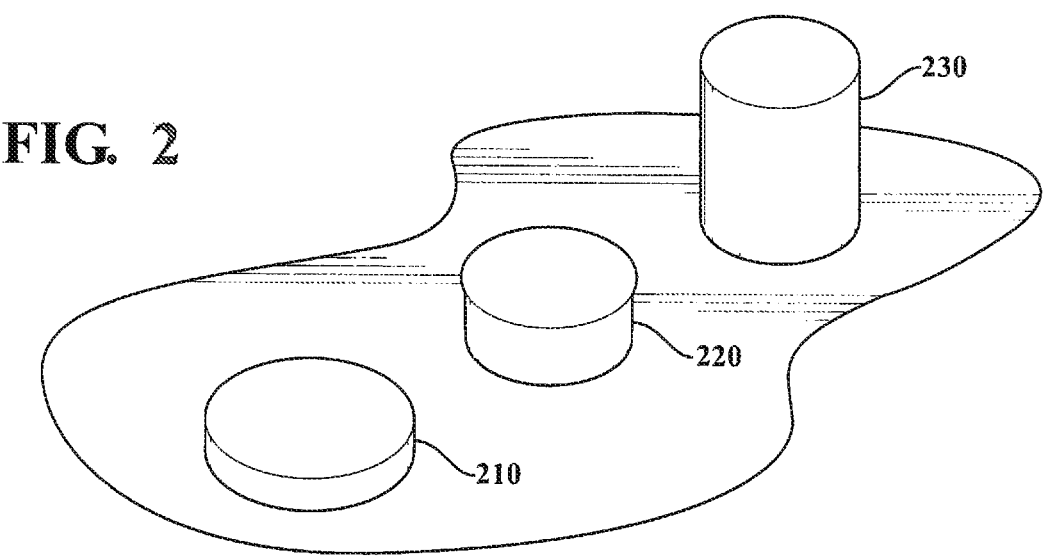
FIG. 2 illustrates examples of carbonated hydroxyapatite cement samples for the EPR dosimetry system of FIG. 1.

FIG. 2 illustrates an example of carbonated hydroxyapatite cement reference source samples for the EPR dosimetry system of FIG. 1. In FIG. 2, three different CHC references sources are shown. A first disc has a diameter of 6 mm and a thickness 2 mm; a second disc has a diameter of 6 mm and a thickness of 4 mm; and a third disc has a diameter of 6 mm and a thickness of 12 mm.

Figure 3:
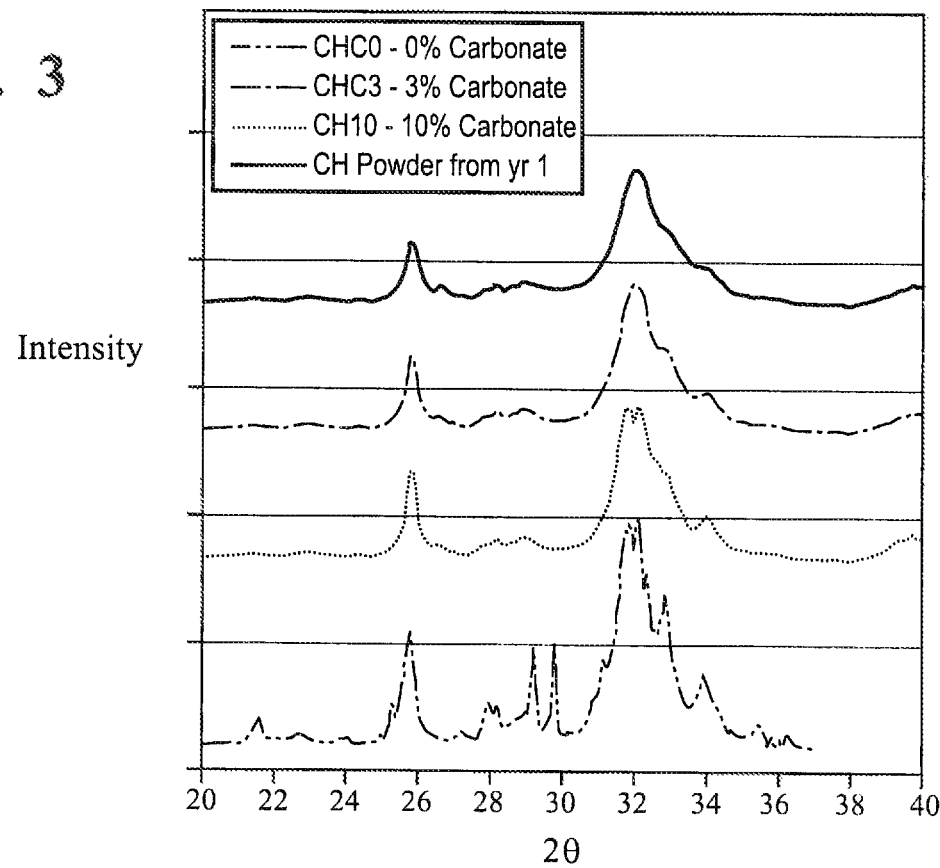
FIG. 3 illustrates XRD patterns of carbonated hydroxyapatite samples with different carbonate content.

FIG. 3 illustrates XRD patterns of carbonated hydroxyapatite samples with different carbonate content. In FIG. 3, XRD patterns are shown for a CH powder produced, for example, by precipitation (the lowest curve in FIG. 3) and, respectively, a CHC sample with 10% carbonate, a CHC sample with 3% carbonate, and a CHC sample with 0% carbonate. The XRD patterns show that all the CHC samples and the CH powder contain low crystalline hydroxyapatite with no unreacted cement or other impurities.

Figure 4:
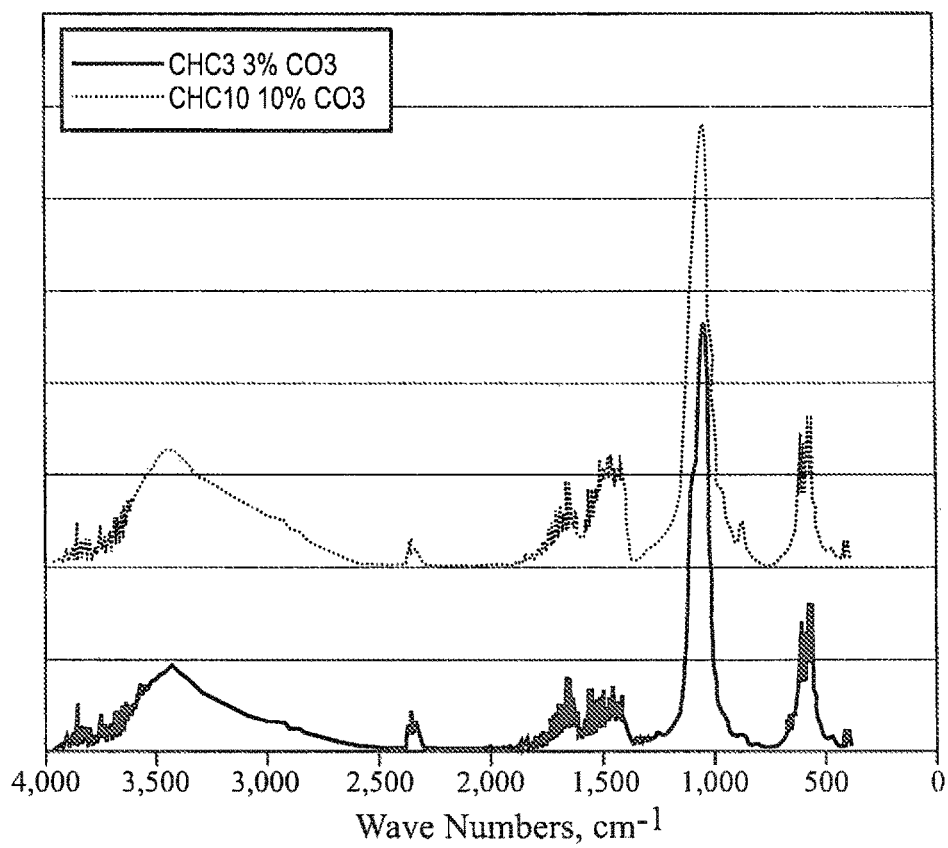
FIG. 4 illustrates FTIR patterns of carbonated hydroxyapatite cement samples with 3% and 10% carbonate contents.

FIG. 4 illustrates FTIR patterns that show that the CHC samples were hydroxyapatite that contained two levels of type-b carbonate similar to apatitic biominerals.

FIG. 5 illustrates an EPR spectrum of a carbonated hydroxyapatite cement reference source sample with 3% carbonate content. As can be seen, the CHC with 3% carbonate produced a spectrally clean example of the radical. The spectrum is free of paramagnetic impurities that were observed in CH powder.

The herein disclosed carbonated hydroxyapatite cements may be used in a dosimeter for the measurement of ionizing radiation absorbed dose. In this situation, the dosimeters may be uniformly mass-produced in a size and shape and shipped to an end user, unirradiated. The dosimeters may be packaged (for example, in a blister pack) and may each be provided a unique identification, such as a bar code or other optical or radiofrequency readout device. The dosimeters may incorporate the herein disclosed cement compositions in a variety of shapes and sizes to address a specific measurement need. Though not a requirement, the addition of a binder may be employed to fabricate a dosimeter of a desired shape for use in a specific application. Such shapes include cylinders (see, for example, FIG. 2), films (either rigid or flexible), or a custom shape or coating to accommodate a specific need.

In an embodiment, such dosimeters may be issued to individuals to serve as personal dosimeters (see FIG. 1).

In another embodiment, such dosimeters may be attached to containers of raw materials (e.g., shrink-wrap films) and/or finished products (e.g., foods or medical devices) that are to receive a high radiation dose with the intent of achieving a desirable effect (e.g., destruction of toxins/microorganisms, or modification of the material's physical properties). After such exposure, the dosimeters are removed and processed using an EPR spectroscopy system to verify the article or package to be irradiated did in fact receive an absorbed radiation dose within the targeted range. As a more specific example, the packaged and identified dosimeters may be attached to containers on a conveyor system that moves the containers past an irradiation source that could be a radioisotope (e.g., Co-60) or an electron beam accelerator of energies between 50 keV and 10 MeV.

FIG. 6 illustrates an exemplary embodiment of the herein disclosed carbonated hydroxyapatite cement (CHC) used as a dosimeter. In FIG. 6, system 600 includes transfer assembly 611, which is used to move packages 601 past radiation source 630. One or more of the packages 601 may have affixed thereon, CHC dosimeter 621, which is packaged in blister pack 620. The CHC dosimeter may be supported on a substrate. The substrate may be imprinted with identification device 623. The identification device may be a barcode, for example.

In another embodiment, by incorporation of sensitizers, the cement compositions may be adapted for a specific dose range (high range for industrial applications; low range for personal dosimetry) or a specific type of ionizing radiation (e.g., neutron radiation). In addition, the cement compositions may incorporate paramagnetic reference materials to improve the accuracy and precision of the absorbed dose measurement.

EPR Biodosimetry with Irradiated CHC as a Reference Source

A large-scale radiation event such as a reactor accident or explosion of a nuclear device has the potential to expose a large population to ionizing radiation. Some members of this population may be minimally exposed and need little if any medical treatment; others may receive a larger exposure, and may require medical treatment; still others may have received so large a dose that medical treatment may not sufficient. Medical emergency response personnel may conduct a triage operation in an effort to identify and adequately treat the maximum number of exposed personnel. Unfortunately, since the population members likely are not being monitored with supplied individual dosimetry, current triage methods may rely on clinical procedures, which may not be able to handle the throughput necessary to assess the entire population. For example, clinical methods may require sample analysis at a remote facility, which in turn may require sample transport and later matching of sample results with the individuals. Alternately, or in addition to clinical analysis, triage methods may rely on field analysis that accesses certain symptoms. These field methods may be very inaccurate. Thus, current triage methods cannot be effectively employed when perhaps many thousands of persons must be evaluated and medical decisions made quickly.

An alternative to current triage methods involves use of biodosimetry. Biodosimetry does not rely on an individual carrying or being in close proximity to a dosimeter. Rather, biodosimetry relies on the fact that certain portions of the human body, when exposed to certain ionizing radiation, can give off a measurable signal that indicates such exposure. Determining or estimating radiation exposure in the case of biodosimetry may rely on electron paramagnetic resonance (EPR). Such resonance provides signals that may be read by a suitable EPR spectrometer.

EPR spectroscopy is a non-destructive technique that may be used to detect and quantify unpaired electrons (e.g., free radicals). The unpaired electrons result from the absorption of ionizing radiation in a target material.

Thus, to determine if an individual has been exposed to ionizing radiation, a device or system such as an EPR spectrometer-based system may be used, in vivo. For example, to determine if a person was exposed to ionizing radiation, as indicated by production of free radicals in the person's teeth, the system may include resonators that are attached to a tooth. The resonators are coupled to a magnet system that effectively encompasses the subject's head.

Dose determination using electron paramagnetic resonance (EPR) spectroscopy of human tooth enamel (EPR biodosimetry) is an established technique for dose reconstruction in radiation accidents during photon irradiation. This technology is based on the fact that ionizing radiation generates unpaired electrons proportional to dose and that, in tooth enamel, these unpaired electron species are extremely stable, persisting for thousands of years. To use this technology, the EPR biodosimeter needs to be calibrated using a set of references that exhibit known and reproducible EPR signals in the desired range. Although tooth enamel is capable of exhibiting stable EPR signals proportional to the ionization irradiation dose, it is not an ideal reference tool for numerous reasons including its non-uniform chemical composition, variable physical properties, and unknown radiation history.

One aspect of EPR dosimetry that remains unresolved is the development and deployment of suitable reference sources for EPR dosimetry readers (i.e., EPR spectrometers). If available, such reference sources could be used to verify proper operation of the EPR spectrometers. To improve EPR dosimetry, especially to improve the integrity of a field-deployed EPR biodosimetry system that determines exposure to population members, disclosed herein is an EPR reference source, method of manufacture, and method of use.

Figure 7:
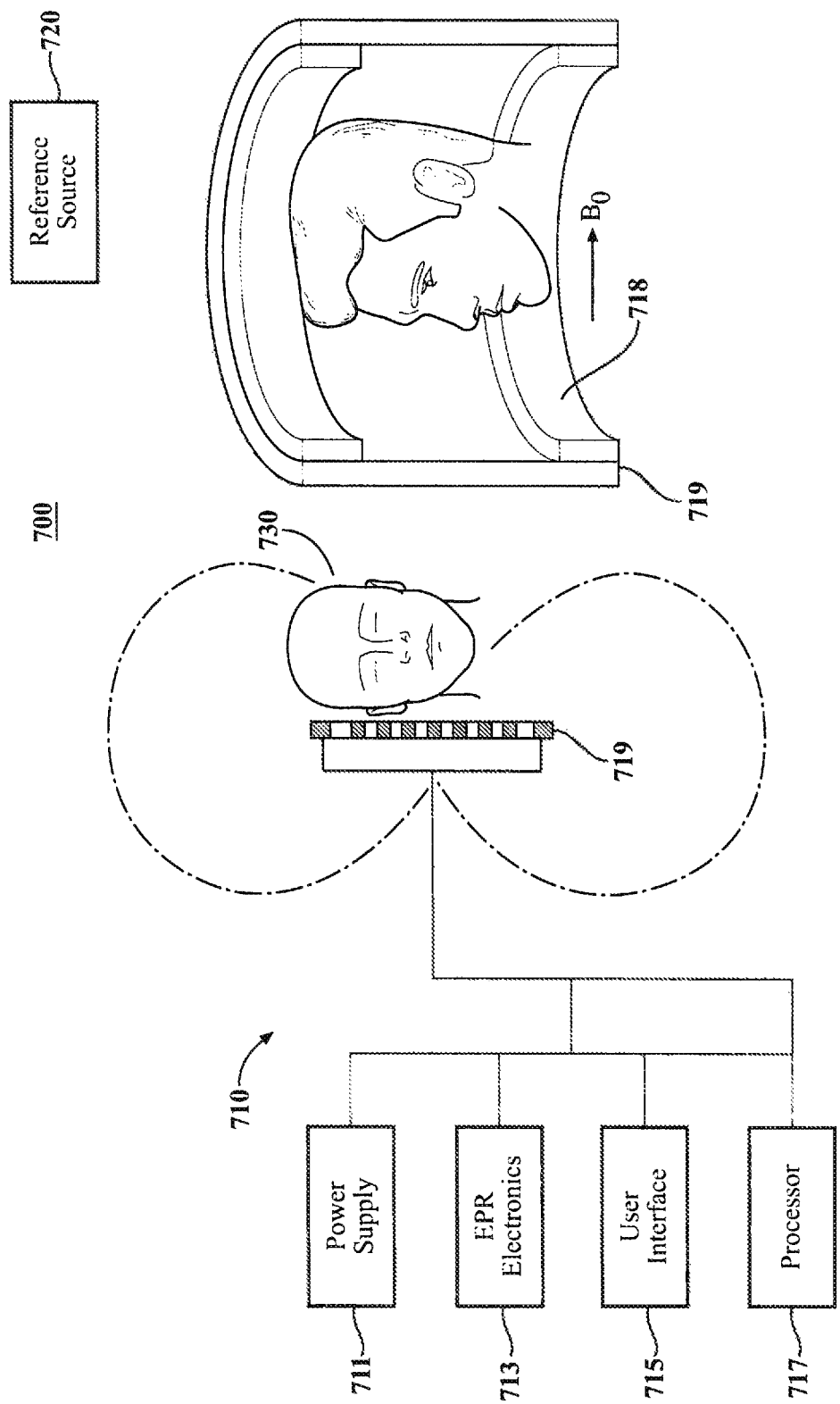
FIG. 7 illustrates carbonated hydroxyapatite used as a reference source for EPR dosimetry.

FIG. 7 is a block diagram of an alternate EPR dosimetry system. In FIG. 7, EPR dosimetry system 700 includes dosimeter reader 710, which in turn includes power supply 711, EPR electronics 713, user interface 715, processor 717, and measurement unit 719. The measurement unit 719 may include a resonator (not shown) that contacts one or more teeth of patient 730. The measurement unit 719 includes a magnet coil section 718 which provides the required magnetic field to induce an EPR signal.

Also shown in FIG. 7 is a reference source 720, which is used to confirm proper operation of the system 710.

In operation, the EPR system 710 may be field-deployed to perform triage operations following a large-scale radiation event. FIG. 7 illustrates one possible configuration of an EPR measurement unit 719. In this configuration the patient's head may be surrounded by, or merely adjacent a set of magnet coils that induce the magnetic field necessary to generate an EPR signal.

The reference source 720 is used to perform an initial check of the system 710, and may thereafter be used to periodically confirm proper operation of the system 710. The reference source 720 may have a form dictated by the system 710. For example, the reference source 720 may have any of the forms shown in FIG. 2.

Prior to shipment to the operator of system 710, the reference source 720 may be irradiated. For example, a certified laboratory may irradiate the reference source 720 using a Co-60 source. After such irradiation, and prior to shipment, the reference source 720 may be tested in the laboratory to verify that it provides the desired EPR signal.

Disclosed above are methods (self-setting cement, sintering) for producing the carbonated hydroxyapatite (CH) crystalline structure used in an example EPR dosimeter. Other methods, including use of other starting components, also may produce a satisfactory crystalline structure for an EPR dosimeter. In particular, methods that result in substantially complete CH formation may be used to produce a satisfactory crystalline structure. In particular, U.S. Pat. No. 5,525,148, incorporated herein by reference, discloses methods for forming a hardened CH mass, In addition to the self-setting cement forming processes described above, a satisfactory carbonate-substituted hydroxyapatite material may be formed by non-cement processes such as those disclosed in the following, which are hereby incorporated by reference:

1. L. G. Ellies, D. G. A. Nelson, J. D. B. Featherstone (1988): Crystallographic structure and surface morphology of sintered carbonated apatites. Journal of Biomedical Materials Research, Volume 22, Issue 6, pages 541-553.
2. Iain R. Gibson and William Bonfield (2002): Novel synthesis and characterization of an AB-type carbonate-substituted hydroxyapatite. Journal of Biomedical Materials Research, Volume 59, Issue 4, pages 697-708.
3. T. S Sampath Kumara, I Manjubalaa, J Gunasekarana (2000): Synthesis of carbonated calcium phosphate ceramics using microwave irradiation. Biomaterials, Volume 21, Issue 16, August 2000, Pages 1623-1629.
4. J. P. Lafona, E. Championa, D. Bemache-Assollantb (2008): Processing of AB-type carbonated hydroxyapatite Ca10-x(PO4)6-x(CO3)x(OH)2-x-2y(CO3)y ceramics with controlled composition. Journal of the European Ceramic Society, Volume 28, Issue 1, Pages 139-147.
5. Michael E. Fleet, Xi Liu (2007): Coupled substitution of type A and B carbonate in sodium-bearing apatite. Biomaterials, Volume 28, Issue 6, Pages 916-926.

We claim:

1. An electron paramagnetic resonance (EPR) device sensitive to emissions from one or both of a gamma radiation emitter and a neutron radiation emitter, comprising:
    an emission-sensitive mass having a crystalline structure, comprising:
        structurally incorporated carbonate content in a range of about 3% by weight to about 10% by weight of the mass
        one or more structurally incorporated non-calcium metallic cations, and
        one or more structurally incorporated phosphate anions; and
    a housing containing the mass.

2. The EPR device of claim 1, wherein the carbonate content is about 3% by weight of the mass.

3. The EPR device of claim 1, wherein the mass is sintered from a carbonated hydroxyapatite powder.

4. The EPR device of claim 1, wherein the mass is formed as a carbonated hydroxyapatite cement.

5. The EPR device of claim 4, wherein the carbonated hydroxyapatite cement is formed by mixing in a ratio of a range of about 0.5 to 5.0 powder-to-liquid ratio:
    a cement powder comprising:
        one or more calcium phosphate compounds, and
        one or more carbonate compounds; and
    a cement liquid comprising a phosphate solution to form a hardened mass.

6. The EPR device of claim 1, wherein the mass is formed using a non-cement process to form a dry product followed by sintering to form a carbonate-substituted hydroxyapatite material.

7. The EPR device of claim 1, wherein the mass is incorporated into a personal dosimeter.

8. The EPR device of claim 1, wherein the mass is irradiated from a known radiation source, whereby the irradiation creates an EPR reference.

9. The EPR device of claim 8, wherein the EPR reference is usable to calibrate an EPR biodosimeter reader.

10. The EPR device of claim 1, wherein the mass further comprises a binder whereby the mass is molded to a desired shape.

11. An emission-sensitive mass having a crystalline structure, comprising:
    structurally incorporated carbonate content in a range of about 3% by weight to about 10% by weight of the mass;
    one or more structurally incorporated non-calcium metallic cations; and
    one or more structurally incorporated phosphate anions.

12. The emission-sensitive mass of claim 11, wherein the carbonate content preferably is about 3% by weight of the mass.

13. The emission-sensitive mass of claim 11, wherein the mass is sintered from a carbonated hydroxyapatite powder.

14. The emission-sensitive mass of claim 11, wherein the mass is formed as a carbonated hydroxyapatite cement.

15. The emission-sensitive mass of claim 11, wherein the carbonated hydroxyapatite cement is formed by mixing in a ratio of a range of about 0.5 to 5.0 powder-to-liquid ratio:
   a cement powder comprising:
      one or more calcium phosphate compounds, and
      one or more carbonate compounds; and
   a cement liquid comprising a phosphate solution.

16. An EPR device, comprising:
   a crystalline, emission-sensitive mass, comprising:
      structurally incorporated carbonate content in a range of about 3% by weight to about 10% by weight of the mass
      one or more structurally incorporated non-calcium metallic cations, and
      one or more structurally incorporated phosphate anions; and
   a housing containing the mass.

17. The EPR device of claim 16, wherein the mass is formed as a self-setting carbonate substituted hydroxyapatite cement.

18. The EPR device of claim 17, wherein the carbonate substituted hydroxyapatite cement is formed by mixing in a ratio of a range of about 0.5 to 5.0 powder-to-liquid ratio:
   a cement powder comprising:
      one or more calcium phosphate compounds, and
      one or more carbonate compounds; and
   a cement liquid comprising a phosphate solution.

19. The EPR device of claim 18, wherein the mass is formed as an EPR dosimeter.

20. The EPR device of claim 18, wherein the mass is irradiated by a known gamma source, and wherein the mass is configured as an EPR reference source.

\* \* \* \* \*

UNITED STATES PATENT AND TRADEMARK OFFICE
CERTIFICATE OF CORRECTION

PATENT NO. : 10,545,214 B2
APPLICATION NO. : 16/431872
DATED : January 28, 2020
INVENTOR(S) : Laurence C. Chow et al.

Page 1 of 1

It is certified that error appears in the above-identified patent and that said Letters Patent is hereby corrected as shown below:

On the Title Page

Item (62) "Division of application No. 15/068,943, filed on Mar. 14, 2016, now abandoned." should read --Division of application No. 15/068,943, filed on Mar. 14, 2016, now U.S. Patent 10,509,092, issued Dec. 17, 2019.--.

In the Specification

Column 1, Line 10, "'Manufacture, and Methods of Use,' which claims priority to" should read --"Manufacture, and Methods of Use," now U.S. Patent 10,509,092, issued December 17, 2019, which claims priority to--.

Column 1, Line 38, "populations groups" should read --population groups--.

Column 2, Lines 23 - 24, "carbonated a hydroxyapatite" should read --a carbonated hydroxyapatite--.

Column 2, Line 32, "Disclosed herein a dosimeter" should read --Disclosed herein is a dosimeter--.

Column 5, Line 6, "references" should read --reference--.

Column 5, Line 8, "a thickness 2 mm" should read --a thickness of 2 mm--.

Column 6, Line 21, "treatment may not" should read --treatment may not be--.

Column 7, Line 65, "hardened CH mass" should read --hardened CH mass.--.

Signed and Sealed this
Sixth Day of October, 2020

Andrei Iancu
*Director of the United States Patent and Trademark Office*